United States Patent [19]

Jackson

[11] 4,026,285
[45] May 31, 1977

[54] HUMIDIFIER FOR AIR TO BE INHALED

[76] Inventor: Richard R. Jackson, 8 Trinity Road, Marblehead, Mass. 01947

[22] Filed: June 2, 1975

[21] Appl. No.: 582,818

Related U.S. Application Data

[63] Continuation-in-part of Ser. No. 241,440, April 5, 1972, abandoned, which is a continuation of Ser. No. 854,427, Sept. 2, 1969, abandoned.

[52] U.S. Cl. .................... 128/192; 128/194; 261/95; 261/149; 261/5
[51] Int. Cl.² ........................... A61M 16/00
[58] Field of Search ............ 128/145.5, 173, 173.2, 128/185, 186, 187, 191, 192, 193, 194, 201, 208, 212; 261/94, 95, 97, 129, 131, 142

[56] References Cited

UNITED STATES PATENTS

| 401,502 | 4/1889 | Krull | 128/192 |
|---|---|---|---|
| 603,021 | 4/1898 | Dight | 128/212 |
| 1,062,750 | 5/1913 | Walker | 128/192 |
| 2,091,034 | 8/1937 | Duncan | 128/192 |
| 2,607,571 | 8/1952 | Hession, Jr. | 128/173 R |
| 3,365,181 | 1/1968 | Schwaneke | 261/142 |
| 3,464,400 | 9/1969 | Wellman | 261/129 |
| 3,534,732 | 10/1970 | Bickford | 128/188 |
| 3,723,707 | 3/1973 | Wunderlin | 261/142 |

Primary Examiner—William E. Kamm

[57] ABSTRACT

A humidifier for air or gas flow to the lungs heats the flow and saturates it with water vapor. Heated water injected into a humidifying passage flows down multiple paths in the gas stream. Heating of the water is shown on a localized basis at sterilizing temperature while over-all temperature is kept lower using a heater combined with the pump of the injection line. All surfaces of the humidifier are shown exposed to the water; the gas outlet connection is shown communicating with a space between the water paths and the reservoir, and directed toward the reservoir; and the humidifying passage is shown as a tubular column holding a mass of tangled inert filaments.

18 Claims, 9 Drawing Figures

FIG 4
Magnified View

HUMIDIFIER FOR AIR TO BE INHALED

This is a continuation in part of application Ser. No. 241,440, filed Apr. 5, 1972, now abandoned, which in turn is a continuation of application Ser. No. 854,427, filed Sept. 2, 1969, now abandoned.

This invention relates to humidifiers for air to be inhaled for use in the hospital with medical respirators and other gas sources during pulmonary ventilation of patients, e.g. during post-operative intensive care, and for use in the home.

A principal object of the invention is to provide improved humidifiers which can have a self-sterilizing effect. Other objects are to provide humidifiers which are effective over a wide range of flow conditions and are of simple and reliable construction.

The humidifiers involved are of the type comprising a water reservoir containing a main charge of water, a gas passage for conducting gas to be inhaled, heater means to heat the water and means for gradually introducing the water into gas in the gas passage from whence it is inhaled. The invention features means for preventing growth of and reducing bacteria in the water comprising means for progressively and temporarily isolating a relatively small quantity of water from the charge of water in the reservoir, the heater means including a heater to heat water in the isolated quantity to a temperature in excess of 140° F, means to allow return of the isolated quantity including the heated water progressively to the main charge of water, and a thermostat energizing and de-energizing the heater means to maintain the temperature of the water introduced in the gas at a temperature substantially less than 140° F, (preferably relatively close to the human body temperature when used e.g. for humidifying respirator air) whereby the humidifier, during extended operation, can prevent growth of and reduce bacteria in the water reservoir without overheating of water entering the gas or the person breathing the thus humidified gas.

In preferred embodiments the isolating means comprises a conduit, with the heater disposed to heat water flowing through the conduit, and the conduit discharging to the reservoir; the isolating means is convection-fed, having inlet and outlet connected to the reservoir below its water level, the inlet positioned lower than the outlet, the heater for heating the isolated quantity effective to produce a convection current, causing heated water to flow from the outlet to the reservoir while relatively unheated water enters from the reservoir through the inlet, and in certain instances preferably a thermostatically controlled valve prevents convection flow of the water through the outlet except when the water reaches a predetermined temperature selected to ensure sterilization of the out-flowing water. In various preferred embodiments the means for introducing the water into gas in the gas passage comprises a nebulizing assembly having its water inlet connected to the reservoir, in certain instances preferably the nebulizer comprising means to produce a high speed jet of oxygen and a venturi water pick-up tube having its inlet in the reservoir and its outlet disposed in the jet, or the means introducing the water to the gas comprises a rotating slinger structure adapted to draw water from the reservoir and sling it to produce fine water particles in the gas passage, or a traveling porous structure is adapted to travel through the reservoir to pick up water and then travel through the gas passage where the water can evaporate from the porous structure and enter the gas stream. Also, in preferred embodiments the humidifier includes means for progressively replenishing the reservoir by a flow exposed to the heater before entering the reservoir, and in certain instances, preferably, the means for isolating the relatively small quantity of water comprises a chamber disposed entirely below the water level of the reservoir, the means for replenishing including a tank having a water level corresponding with that of the reservoir, and the tank having a connection to the bottom of the chamber whereby, when water is drawn from the reservoir tending to lower its water level, gravity flow occurs from the tank, although the chamber and thence to the reservoir.

According to another feature of the invention a humidifying passage is located above a reservoir, into which is injected a stream of warmed water which falls through multiple flow paths defined in the gas stream, these paths preferably being defined by a tubular column holding a mass of tangled filaments. Heating of the water is featured on a localized basis with the heater surface-maintained at a higher temperature than the general temperature of the water. Here again, with the heater surface heated to a sterilizing temperature, a local sterilizing effect can occur which, during prolonged operation, can be effective to reduce contamination or to sterilize the system. Advantageously the heater and the pump of the injection line are combined and all surfaces in the humidifier are exposed to the thus-treated water.

The invention also features a humidifier of the general construction as described, with the gas outlet connection located below the water paths, in a space provided above the water level in the reservoir, and directed toward the reservoir.

These and other objects and features will be understood from the following detailed description of preferred embodiments wherein:

Figures 1, 2, 3, 4, 5:
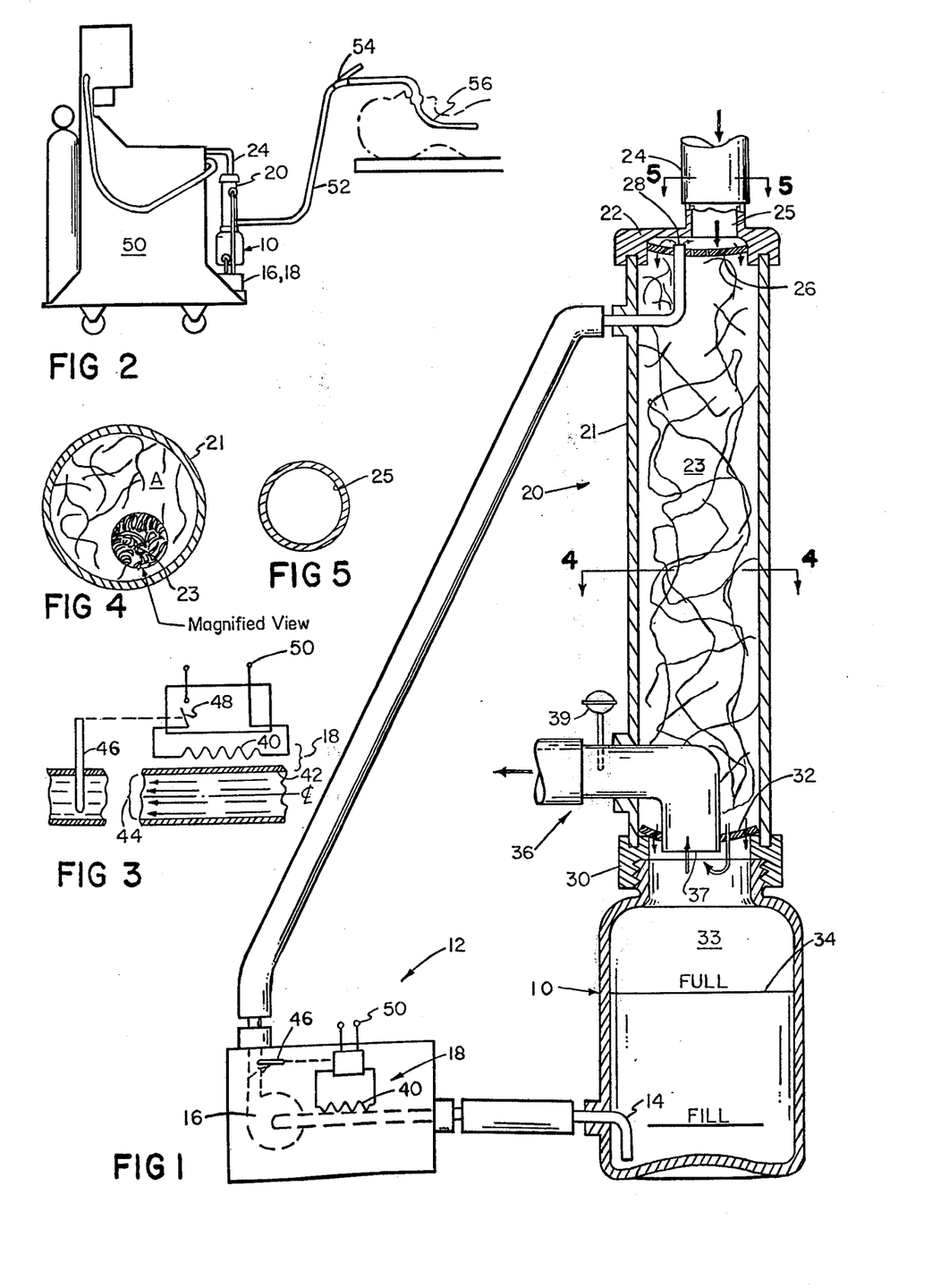
FIG. 1 is a side view, partly in cross-section of a preferred embodiment of the invention.
FIG. 2 is a diagrammatic view of the humidifer of FIG. 1 in use with a respirator.
FIG. 3 is a diagrammatic view of the heating unit of the embodiment of FIG. 1.
FIGS. 4 and 5 are cross-sectional views taken on lines 4—4 and 5—5 of FIG. 1, and FIGS. 6, 7, 8 and 9 are side views, partly in cross-section of differing preferred embodiments of the invention.

Referring to FIG. 1 reservoir 10, in the form of a mason jar, is connected to injection line 12 through water intake connection 14. Combined pump 16 and heater 18 pump and heat the water and inject it into the top of humidifying passage 20.

In this embodiment humidifying passage 20 comprises a 1½ inch internal diameter pipe 21 filled with a mass of stable inert filaments 23, such as the tangled metal filaments of kitchen scrub pads, known under the trademark "Chore Girl". At the top of the column a fitting 22 serves to connect the air supply hose 24 to tubular column 21 and to retain water distribution plate 26. The outlet 28 of water injection line 12 extends above this plate 26 and its stream of water is directed upwardly against the inner surface of fitting 22, thence spreads across the distribution plate 26, falls through its multiple holes and trickles through the multitude of flow paths defined by the filaments, downwardly to the reservoir.

A lower fitting 30 serves to join the tube 21 to the reservoir 10 and to retain lower perforated plate 32. The latter retains the filaments 23. A space or plenum 33 is defined in the jar between the predetermined "full" level 34 inscribed on the jar and plate 32 which marks the end of the multiple flow paths. Gas outlet 36 is secured to the lower end of tube 21 and extends downwardly through lower plate 32 into space 33, with its opening 37 directed downwardly toward the water in the reservoir. Thus constructed it is found that harmful carry-over of water particles by the gas flow is avoided. This gas flow proceeds down the column through the filaments and into plenum 33, and must receive direction to enter gas outlet opening 37 to proceed to the patient; also in this position the outlet piping is exposed to the trickling water, for a washing effect to be described.

All surfaces in the humidifier advantageously are formed of impervious, inert and wettable material, to permit effective washing action by the water. A thermometer 39 reads the temperature of gas in outlet 36.

Referring to the diagram of FIG. 3 as well as to FIG. 1 heater 18 comprises a resistance heater element 40 associated with a heater surface 42. With the element energized, heater surface 42 can become quite hot to establish a thermal gradient across the cross-section of the immediately adjacent portion of water stream 44, from a high temperature at the heater surface 42 to a lower temperature inwardly toward the stream centerline. As illustrated, downstream of the heater, a thermal sensor, indicated as probe 46, reads a more general or average temperature of the stream and on that basis controls the activation and deactivation of the heater element through switch 48 and power supply 50.

Referring to FIG. 2 as well as FIG. 1, during operation gas from a gas source, e.g. air under controlled pressure and volume from respirator 50, is introduced through inlet hose 24 and gas connection 25 into the top of tubular column 21. From there the gas proceeds, under the force of the respirator down the length of the column thence out the outlet connection 36, and through hose 52 and valve 54 to endotracheal tube 56. As is well known, expiration proceeds to atmosphere through the other leg of check valve 54.

As the gas stream proceeds down tube 21 the gas encounters a large aggregate area warm water interface formed by the tangled filaments 23. The cross-section area of the tube A, FIG. 4, is suitably larger than the cross-section of inlet hose 24, FIG. 5, that taking into account the mass of filaments 23, there is ample airflow cross-section and exceedingly little resistance to air flow is presented. This is true despite the fact that the multitude of tangled filaments dispersed across the tube are effective to split the gas stream into a similar multitude of tortuous gas streams. This is achieved for example with the air hoses 24 and 54 and connections of ¾ inch ID, the tube 1½ inch ID and having a filled length of 8 inches, with four "Chore Girl" pads of brass or stainless steel inserted over that length (weighing in aggregate approximately 6 ounces).

The effect of the humidifier described is to kill bacteria and improve sterility over time. Ordinarily 15 minutes warm-up operation of the humidifier is satisfactory to produce a measurable sterilizing effect in the humidifier.

EXAMPLE I

The humidifier as described was equipped with a pump-heater combination known as the Gorman-Rupp Aquamatic Heating Pad Pump with heater rated at 225 watts, having a brass pump housing with resistance heater element in heat-conducting relation with a water-contacting surface thereof, and operable to maintain a flow rate of 6–8 L/m in the water injection line.

The humidifier was gas sterilized and aerated in a vacuum cleaner with air flow overnight. It was filled with sterle water into which was injected 1 c.c. of a 24 hour broth culture containing heat-resistant enterococci. Pump and heater were energized with no air flow through the humidifier. Sterilized syringe and needle were used to withdraw samples periodically from the water. The samples were placed in closed petri dishes with melted agar added, placed in incubator and examined in 24 hours and 48 hours, using a scale of 4, in which 4 represents colonies present in number too numerous to count by naked eye. Results:

| time for injection, | Result of Examination | |
| minutes | 24 hours | 48 hours |
| --- | --- | --- |
| 5 | 4+ | 4+ |
| 10 | 3+ | 3+ |
| 15 | 1+ | 1+ |
| 30 | few | few |
| 60 | 0 | 1 colony |

By visual judgement of the experimenter, a bacteriologist, the effect of operation of the humidifier was to produce a gradual reduction of bacteria present in the water over time.

EXAMPLE II

A 3 c.c. mixture was prepared, 2 c.c. sterile water and 1 c.c. of 24 hour culture broth of staphyloccus-albus, a strain not so temperature resistant as the previous example.

The mixture was inserted in a Vaponefrin Nebulizer creating a contaminated gas jet, with a steady flow of oxygen into the device.

The output of the device was exposed for 1 second to a blood agar plate, which after being incubated overnight showed colonies completely covering the plate, 4+ on the scale as above.

The outlet of the Vaponefrin was connected to inlet 25 of the humidifier, previously sterilized as above, and the device was operated in excess of one half minute.

The water was sampled as in Example I using blood agar plates. Also a respirator was operated at sample times and six puffs (approximately six liters) were directed at different spots on sample plates. The colonies were counted after 24 hours incubation.

Results

| time from injection, | Result of Examination | |
| minutes | Water | Gas |
| --- | --- | --- |
| 5 | 70 | 5 |
| 10 | 17 | 3 |
| 15 | 5 | 0 |
| 30 | 0 | 0 |
| 60 | 0 | 0 |

EXAMPLE III

The procedure of Example II was repeated, with the pump running but with the heater turned off.

| time from injection, minutes | Water | Gas |
|---|---|---|
| 1 | Moderate number | 0 |
| 5 | Minor reduction | 26 |
| 10 | Minor reduction | 5 |
| 15 | Minor reduction | 2 |
| 30 | 15 | 0 |
| 60 | 17 | 0 |

Dew point tests of the output of the humidifier and of the hose connection to the patient have shown saturation with water vapor over the entire range of flow rates, ranging in minute volumes from normal of 5 to 6 liters per minute up to 20 liters per minute, delivered at various representative breath rates.

In use with patients, secretions of the upper respiratory tract have been thin and fluid, indicative of proper humidification of that region. Proper patient triggering of volume limited respirators through the humidifiers have been observed repeatedly.

The water from humidifiers being used for prolonged ventilation of patients under intensive care have been sampled repeatedly. Each sample has been sterile, indicating the lack of need each day to change the gas inlet hoses, as has previously been customary.

Figure 6:
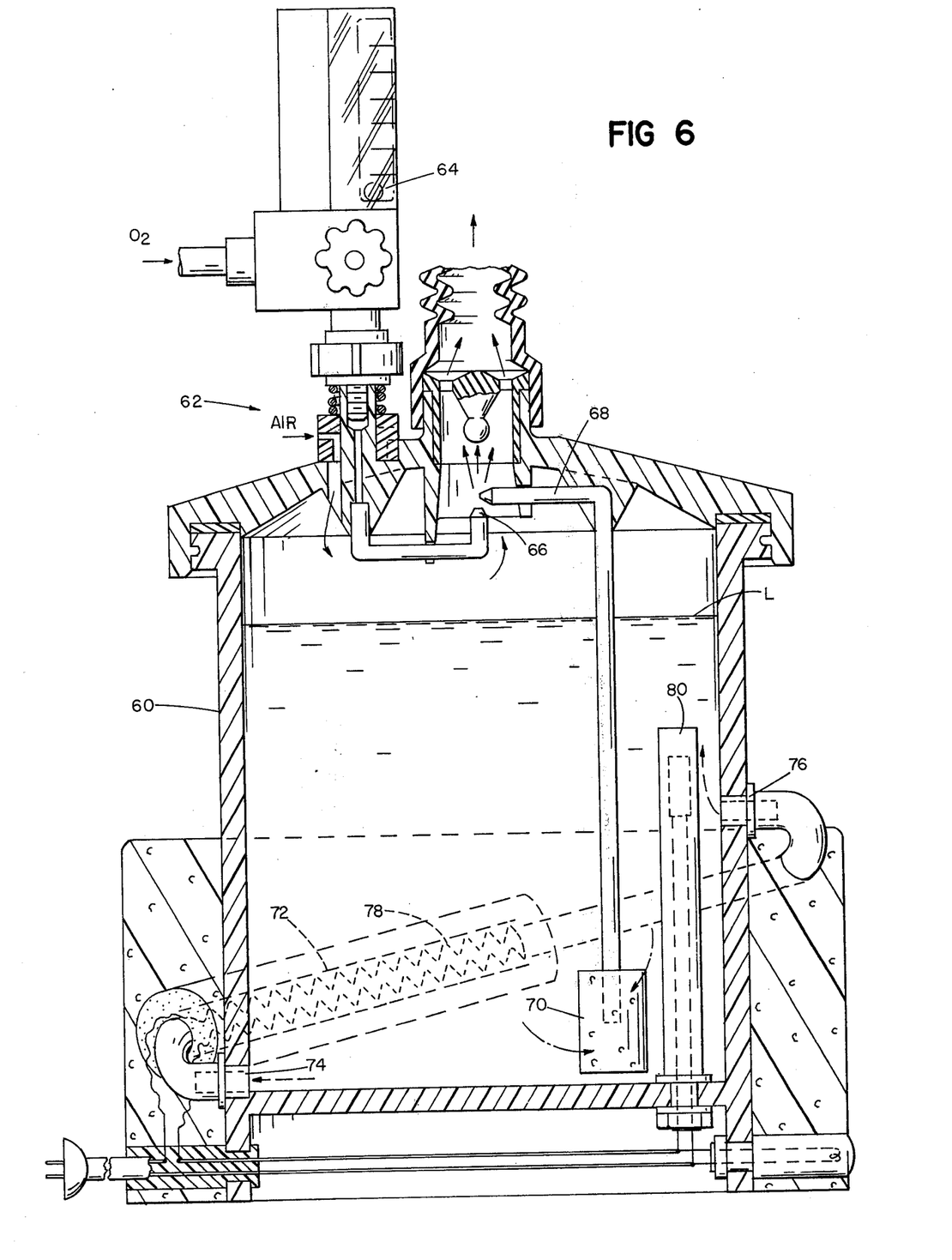

According to the further embodiment of FIG. 6, a reservoir 60 of water is associated with a nebulizing assembly 62 which receives oxygen under pressure through regulator 64, produces a high speed oxygen jet through nozzles 66, and induces a flow of water by venturi effect of the gas jet at the outlet of water pick-up pipe 68, inlet 70 of which is at the bottom of the reservoir. The gas jet has the conventional effects of reducing the water to small particle size dispersed in the gas flow and drawing air into the flow at a percentage dependent upon the setting of the air inlet opening.

A conduit 72, surrounded by thermal insulation, has inlet 74 connected to the bottom of the reservoir and slants upwardly to outlet 76 at a higher level, though below the water level L of the reservoir. Heater 78 is disposed to heat the water for the same effect as described for the embodiment of FIGS. 1-5, but in this case convection flow is relied upon, rather than a pump, for causing the water to circulate. When heated to sterilizing temperature, the water, by virtue of reduced density, rises and flows out of outlet 76 while cooler water to be treated enters inlet 74, in a progressive way. Thermostat 80 senses the general temperature of water in the reservoir 60, activating and deactivating heater 78 in the manner to keep the main charge within the desired temperature limits, below the sterilizing temperature.

Figure 7:
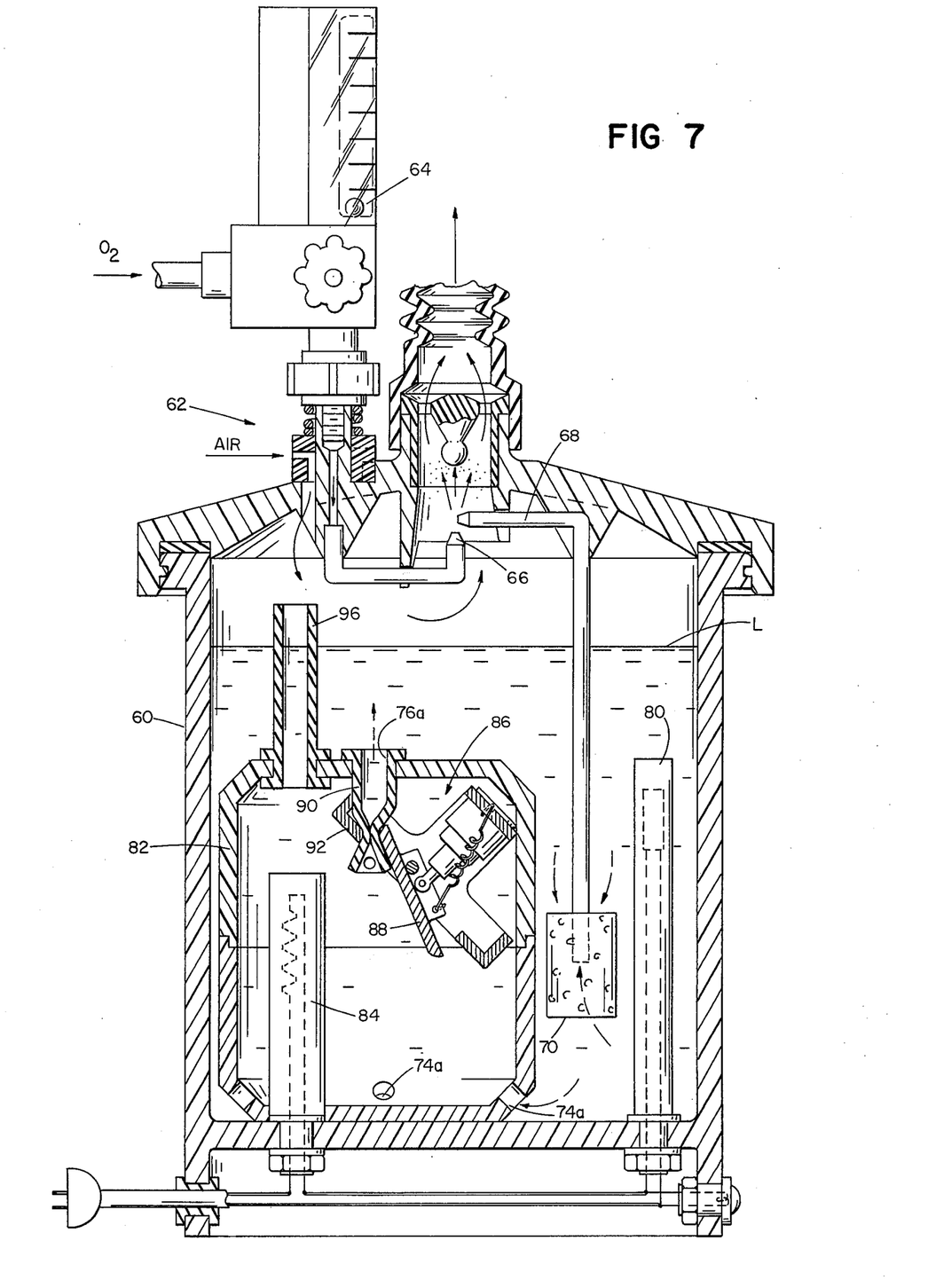

The embodiment of FIG. 7 is similar to that of FIG. 6 regarding the nebulizing assembly and thermostatic control of the heater, however the convection-fed conduit is replaced by a convection-fed isolation chamber 82 disposed below the water level L of the reservoir, with inlet 74a at the bottom of the chamber and outlet 76a at the top. Heater 84 is disposed within the chamber. To ensure that the isolated water is subjected to sterilizing conditions a thermostatically operated valve 86 is provided at the top of chamber 82. In the embodiment shown a conventional automotive radiator thermostat valve 88, with opening temperature of e.g. 195° F and closing temperature e.g. of 190° F is employed to open and close by pinch of tube 90, against abutment 92. By this means it is assured that water in the reservoir 82 reaches a temperature above e.g. 190° F before being returned to the reservoir. The relationship of the heating capacity of the heater to the thermal capacity of the isolated volume of the water is chosen to assure that the water is at temperature above 140° F for a prolonged period (as it heats from 140° to 190° F) to assure kill of the more heat-resistant organisms.

For example the volume of reservoir 60 may be 600 ml, the thermostat 80 may be designed to maintain a temperature therein of about 100° F, the volume of the isolation chamber 82 may be 180 ml, and the heater may be rated at 75 or 100 watts.

A vent 96 is provided to release any gas or dissolved air that is produced during operation of the heater, thus to ensure that the isolation chamber remains full at all times and that convection flow takes place.

A demonstration of this self-sterilizing humidifier employed a 24-hour broth culture of Enterococci, which is a heat-resistant (killed at 60° C in 30 minutes) gram-positive coccus. Cultures were taken of the water in the reservoir and the aerosol emitted from the humidifier to determine the rate of kill of the test organism.

Results: After adding the broth culture of enterococci and turning on the humidifier, the temperature of the isolation chamber 82 rose to 95° C and of reservoir 60 to 37° C.

The following observations were made:

| EXPOSURE TIME | CULTURE OF $H_2O$ | CULTURE OF AEROSOL |
|---|---|---|
| 1 minute | 4+ (confluent growth) | 1+ |
| 30 minutes | 3+ | less than 1+ (14 colonies) |
| 60 minutes | 1+ | less than 1+ (4 colonies) |
| 90 minutes | less than 1+ (7 colonies) | no growth |
| 120 minutes | no growth | no growth |

At the end of the experiment, a swab culture of the inner surface of the opening of the humidifier at the hose juncture was taken and found to be positive (2+).

Conclusion: This experiment demonstrates the effective killing of the test bacteria (enterococci) in the humidifier water. The killing occurred within 30 minutes and as the water circulated due to conversion, the killing effect continued until at 2 hours' time no viable organisms were found in the water reservoir or the aerosol.

The culture of the inner surface of the delivery opening indicates that organisms may collect in droplets on these inner surfaces but these would eventually fall into the reservoir and be killed.

Figure 8:
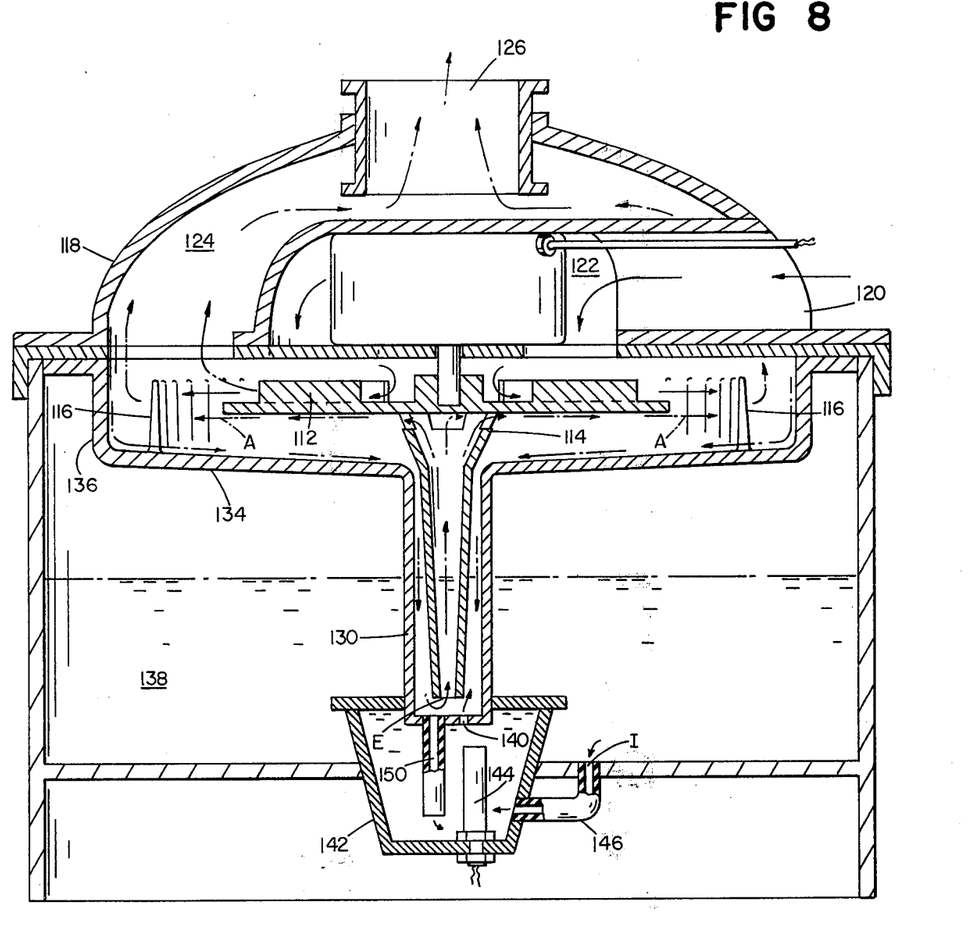
Figure 9:
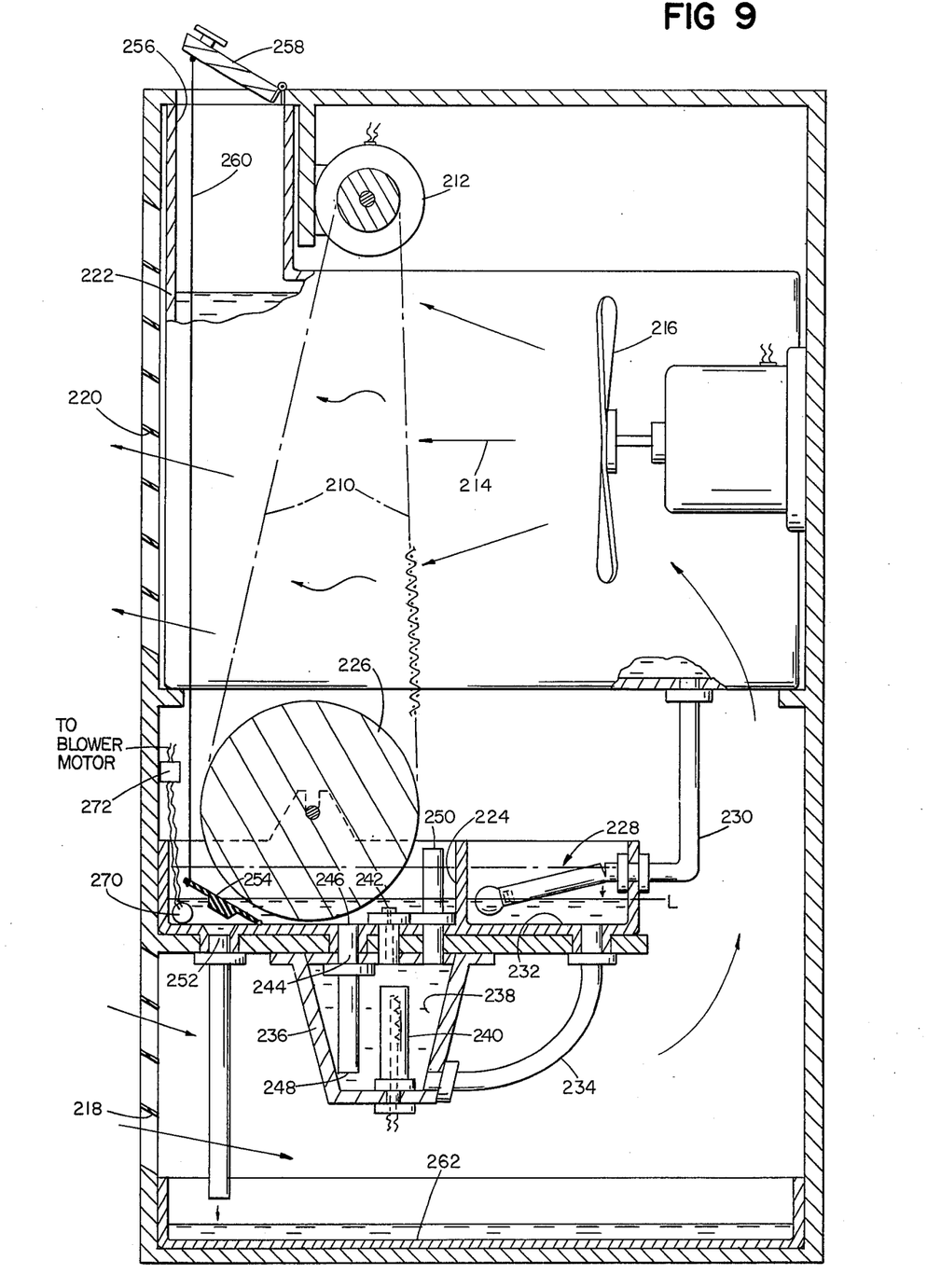

The embodiment of FIG. 8 is a slinger-type humidifier. In this type an impeller slings water centrifugally against a breakup structure, for instance in the shape of an annular comb, dividing the water into mist particles. Air flowing past the comb picks up the mist particles and proceeds to the point of use. A large percentage of the water slung to the comb returns to the reservoir while a small percentage passes to the patient or the room being humidified. In prior such humidifiers the returned water, having picked up organisms from the air, introduces these to the reservoir where they can multiply. In time water taken from the reservoir introduces increased amounts of organism to the airflow.

The invention overcomes this problem by capturing and funneling bacteria-exposed return water from the comb back to a reservoir of reduced size from which the supply to the slinger is drawn. Means are provided to sterilize water from a make-up tank as it enters the reservoir and the water in the reservoir is subjected to sterilization on a progressive basis employing principles previously described.

Referring to FIG. 8 slinger 112 of conventional design draws water through rotating pickup tube 114 and slings the water in direction of arrows A against a water breakup comb-like structure 116, water striking the structure being broken into small mist droplets. These droplets are confined to air duct 118 through which air proceeds via entry 120 and annular distribution path 122. The air, after being exposed to the water mist, proceeds through exit duct 124 and outlet 126 to the patient. The pickup tube 114 has water entrance end E in a cylindrical reservoir 130. At the upper end the cylindrical reservoir flares to form bottom collection wall 134 and side collection wall 136, together collecting all water dropping downwardly from comb 116, thus intercepting the water from direct fall to the supply tank 138. Combined structure 134 and 136 returns this water to reservoir 130 where it is again sucked up through entrance E of the rotating pickup tube 114 and delivered to the slinger. The entry 140 of water into the reservoir is from isolation chamber 142 which contains a heater 144 with thermostatic control not shown, water entering this chamber through duct 146 connected to the supply tank at inlet I and discharging to the bottom of the chamber 142 as shown. By operation of the heater under thermostatic control the temperature of the water at the upper part of the heater chamber is maintained at approximately 190° F and all water entering through inlet I from the supply tank is heated to this temperature before it has an opportunity to enter the isolated chamber, thus being initially sterilized and effectively maintaining the slinger structure sterile too.

The water levels within the supply tank 138 and the reservoir 130 are kept even due to gravity flow. Additionally convection flow of the water occurs from reservoir 130 down through tube 150 to a lower region of the isolation chamber 142 from which it is again heated and passes through outlet 140, and thus the contents of the reservoir 130 are subject to sterilizing conditions in a progressive way.

Referring to the embodiment of FIG. 9, a moving belt humidifier is shown comprising an endless moving belt 210 driven by motor 212 carrying a wetted, air-permeable belt across an airflow path 214 produced by blower 216 drawing air from inlet 218 and expelling the air, after passage through the belt, through outlet 220 into the room to be humidified. A supply tank 222 is located alongside the belt, storing for instance 3–5 gallons of water. A pickup reservoir 224 is provided at the lower pulley 226 which carries the belt through a shallow depth of water for continual wetting of the belt. The level of water in reservoir 224 is maintained by float valve 228 controlling the flow of water from supply tank 222 through duct 230. The water that is discharged by float valve 228 enters separate compartment 232 which is connected to the reservoir 224 through duct 234 and chamber 236. The chamber 236 defines an isolated volume 238 containing a heater 240. An outlet orifice 242 is positioned to receive water from the top of the volume 238, i.e. water which is the hottest and has the least specific gravity. A recirculation inlet line 244 has its inlet 246 at the bottom of the reservoir 224 and its outlet 248 at the bottom of the heater tank 236. Also an atmospheric vent 250 is provided with outlet located above the water level in the reservoir and inlet located at the top of the chamber 236.

The reservoir 224 is provided with a discharge outlet 252 having a flapper valve 254 and the supply tank 22 is provided with a fill opening 256 covered by flap 258. Flap 258 and flapper valve 254 are connected by tension cord 260 in the manner that opening flap 258 to admit a new charge of water simultaneously opens flapper valve 254 to dump the contents of the reservoir 228 containing concentrated salts. The contents thus dumped enter evaporator pan 262, air entering through entry 218 flowing across this evaporator pan to gradually evaporate the liquid, leaving a deposit of salts behind which can at long intervals be removed.

A heater 270 is provided also in the reservoir 224, below water level L. This heater is connected to timer 272.

In operation as the level of water in reservoir 224 goes below design level L, float valve 228 opens, discharging water to tank 232. Water then flows by gravity through tube 234 and the isolation chamber 236 to equilibrate the water level with the reservoir. That water which enters the reservoir 224 flows from the top of the chamber 236 and therefore is the hottest water. The heater 240 in the heater chamber 236 is set to maintain a temperature of 180°–190° F. at the top of the chamber. Thus all water entering from compartment 232 is exposed to such temperature for a period permitting sterilization. When the valve 228 is closed, flow continuous from the chamber 236 through the orifice 242 into the reservoir 224 by convection effects, the chamber 236 being kept full by colder water entering the chamber through recirculation line 244, from the bottom of the reservoir through entrance 246. In this manner organisms arriving in the reservoir due to pickup by the belt from the airflow and transfer as the belt enters the water in the reservoir is, on a statistical basis, killed. Periodically a more complete sterilization of the reservoir 224 and belt 210 is accomplished by operation of heater 270. Timer 272 operates the heater 270 for 15 minutes every 12-hour period. At such time that the timer turns on the heater 270 and it turns off the blower 216, thus preventing evaporative cooling of the belt and lowering of the temperature of the belt and the water through which it passes. The design rating of heater 270 may be one thousand watts to bring the water in the reservoir near to or above boiling for sterilizing purposes. During such energization of heater 270, the belt 210 is operated, thus being immersed in the hot sterilizing water and killing any bacteria which have grown on the belt itself.

At the time of filling, when flap 258 is opened to admit water to the supply tank 222, the coupled flapper valve 254 is lifted, draining the reservoir 224 and thus removing water containing an increased amount of solid salts that are present due to the evaporation process.

Advantageously, the float valve is, as shown, in the form of a piece of silicon rubber tubing slit more than half way, enabling flow of low pressure water from the supply tank 222 into tank 232 due to hinged flexing of the tube downwardly as shown in FIG. 9.

Numerous modifications of the specific details are within the spirit and scope of the invention.

What is claimed is:

1. In a humidifier for use with a medical respirator or other gas source, comprising a water reservoir containing a main charge of water, a gas passage for conducting gas to be inhaled by a person, heater means to heat said water and means for gradually introducing said water into gas in said gas passage from whence it is inhaled by the person, the improvement including means for preventing growth of and reducing bacteria in said water comprising means for progressively and temporarily isolating a relatively small quantity of water from the charge of water in said reservoir, said heater means including a heater to heat water in said isolated quantity to a temperature in excess of 140° F, means to allow return of said isolated quantity including said heated water progressively to said main charge of water, and a thermostat energizing and de-energizing said heater means to maintain the temperature of the water introduced in said gas at a temperature substantially less than 140° F whereby said humidifier, during extended operation, can prevent growth of and reduce bacteria in said water reservoir without overheating of water entering said gas or the person breathing the thus humidified gas.

2. The humidifier of claim 1 wherein said means for progressively and temporarily isolating said relatively small quantity of water comprises a conduit, said heater dispensed to heat water flowing through said conduit, and said conduit discharging to said reservoir.

3. The humidifier of claim 1 wherein said means for progressively and temporarily isolating said small quantity of water is convection-fed, having an inlet and an outlet connected to said reservoir below the water level thereof, said inlet positioned lower than said outlet, said heater for heating said isolated quantity effective to produce a convection current, causing heated water to flow from said outlet to said reservoir while relatively unheated water enters from said reservoir through said inlet.

4. The humidifier of claim 3 including a thermostatically controlled valve preventing flow of said water through said outlet except when the water reaches a predetermined temperature selected to ensure sterilization of said out-flowing water.

5. The humidifier of claim 1 wherein said means for introducing said water into gas in said gas passage comprises a nebulizing assembly having its water inlet connected to said reservoir containing sterilized water.

6. The humidifier of claim 5 wherein said nebulizer comprises means to produce a high speed jet of oxygen and a venturi water pick-up tube having its inlet in said reservoir containing sterilized water and its outlet disposed in said jet.

7. The humidifier of claim 1 wherein a rotating slinger structure is adapted to draw sterilized water from said reservoir and sling it to produce fine water particles in said gas passage.

8. The humidifier of claim 1 wherein a traveling porous structure is adapted to travel through said reservoir to pick up sterilized traveling water and then travel through said gas passage where said water can evaporate from said porous structure and enter the gas stream.

9. The humidifier of claim 1 including means for progressively replenishing said reservoir by a flow exposed to said heater before entering said reservoir.

10. The humidifier of claim 9 wherein said means for progressively and temporarily isolating said relatively small quantity of water comprises a chamber disposed entirely below the water level of said reservoir, said means for replenishing including a tank having a water level corresponding with that of said reservoir, said tank having a connection to the bottom of said chamber whereby, when water is drawn from said reservoir tending to lower its water level, gravity flow occurs from said tank, through said chamber and thence to said reservoir.

11. The humidifier of claim 1 for use for example to humidify gas introduced directly to a medical patient via an endotracheal tube wherein said thermostat is adapted to maintain the temperature of the water introduced in said gas at a temperature relatively close to the human body temperature.

12. For use with a medical respirator or other gas source that introduces gas to lungs for a living being, a medical humidifier for saturating the gas with water vapor at a temperature near body temperature, said humidifier comprising a water reservoir, a humidifying passage, said passage disposed above and communicating at one end with said reservoir, gas inlet and gas outlet connections at opposite ends of said passage, a water injection line including a pump connected to withdraw a stream of water from said reservoir and introduce it to the humidifying passage, a heater having a heater surface located at a point along said water injection line and adapted to heat that portion of the water stream that comes in contact therewith as the stream flows by, a thermostat for energizing the heater on the basis of the general temperature of the water stream spaced downstream from said heater, and means defining multiple water flow paths in said humidifying passage for the water from said injection line to return to said reservoir, said paths dispersed through the gas flow path in said passage providing a warm water-to-gas interface to humidify the gas flow to said patient.

13. The humidifier of claim 12 wherein said heater and said pump are combined, one of the water-containing surfaces of said pump comprising said heater surface and adapted to be heated by such heater to temperatures in excess of 140° F, and said thermostat adapted to maintain the general temperature of said stream leaving said pump at a temperature substantially less than 140° F.

14. The humidifier of claim 12 wherein said reservoir has a full water level, a plenum space is defined above the full water level of said reservoir and below said humidifying passage and the gas outlet connection communicates with said plenum through an opening directed toward said reservoir.

15. The humidifier of claim 12 wherein said means defining multiple flow paths comprises a mass of tangled inert filaments confined within said humidifying passage.

16. The humidifier of claim 15 wherein said reservoir has a full water level, said humifying passage comprises a column filling with said filaments and the gas outlet connection communicates with the space between the filled column and the full water level of said reservoir.

17. The humidifier of claim 12 having a hollow vertical tube, said humidifying passage is defined by said hollow vertical tube, said tube releasably secured at its lower end to said reservoir.

18. The humidifier of claim 12 wherein the outlet of said water injection line to said humidifying passage is positioned at the top of said passage and all components of said humidifier exposed to contact by air flowing therethrough are exposed to water from said injection line as it travels back to said reservoir.

* * * * *

UNITED STATES PATENT AND TRADEMARK OFFICE
CERTIFICATE OF CORRECTION

PATENT NO. : 4,026,285
DATED : May 31, 1977
INVENTOR(S) : Richard R. Jackson

It is certified that error appears in the above-identified patent and that said Letters Patent are hereby corrected as shown below:

Col. 2, line 14, "although" should be --through--;

Col. 3, line 16, "receive" should be --reverse--;

Col. 8, line 9, "22" should be ---222--;

" " line 35, "continuous" should be --continues--;

" 10, line 15, "for" should be --of--;

" 10, line 40, "temperatures" should be --temperature--.

Signed and Sealed this

Twenty-eighth Day of February 1978

[SEAL]

Attest:

RUTH C. MASON
Attesting Officer

LUTRELLE F. PARKER
Acting Commissioner of Patents and Trademarks